United States Patent
Jegorov et al.

(10) Patent No.: US 6,235,017 B1
(45) Date of Patent: May 22, 2001

(54) DEVICE FOR ABLATION OF MATERIAL BY MEANS OF LASER RADIATION

(75) Inventors: Valeriy Jurevich Jegorov; Aleksey Fyodorovich Kornev; Igor Alexejevich Mironov; Aleksey Alekseyevich Nikitichev; Guriy Timofeyevich Petrovskiy, all of St. Petersburg (RU); Hans-Joachim Pohl, Jena (DE); Vasiliy Petrovich Pokrovskiy, St. Petersburg (RU); Vladimir Michailovich Reiterov, St. Petersburg (RU); Leonid Nikoljevich Soms, St. Petersburg (RU); Rudolf Steiner, Ulm (DE); Vladimir Konstantinovich Stupnikov; Aleksandra Mikhailovna Tkachuk, both of St. Petersburg (RU)

(73) Assignee: VITCON Projektconsult GmbH, Jena (DE)

( * ) Notice: Subject to any disclaimer, the term of this patent is extended or adjusted under 35 U.S.C. 154(b) by 0 days.

(21) Appl. No.: 09/180,535

(22) PCT Filed: Mar. 7, 1998

(86) PCT No.: PCT/EP98/01349

§ 371 Date: Jan. 13, 1999

§ 102(e) Date: Jan. 13, 1999

(87) PCT Pub. No.: WO98/40940

PCT Pub. Date: Sep. 17, 1998

(30) Foreign Application Priority Data

Mar. 11, 1997 (DE) ............................................. 197 09 861

(51) Int. Cl.$^7$ .................................................... A61B 18/18

(52) U.S. Cl. .................. 606/16; 606/9; 606/13; 372/39

(58) Field of Search ...................... 219/121.6, 121.74; 372/2–4, 22, 26, 39–41; 505/181–183, 191; 331/94.1, 107 R

(56) References Cited

U.S. PATENT DOCUMENTS

| | | | |
|---|---|---|---|
| 4,597,638 | * | 7/1986 | Chemla et al. ...................... 350/354 |
| 4,852,567 | * | 8/1989 | Sinofsky ............................ 128/303.1 |
| 5,147,354 | * | 9/1992 | Boutacoff et al. ...................... 606/15 |

(List continued on next page.)

FOREIGN PATENT DOCUMENTS

| | | |
|---|---|---|
| 43 41 108 | 6/1995 | (DE) . |
| 195 07 939 | 8/1996 | (DE) . |
| 0 444 949 | 9/1991 | (EP) . |

OTHER PUBLICATIONS

XP–002072238 "Luminescence and Induced Emission Lithium–Erbium and Lithium–Holmium Binary Florides" Morozov, et al (Optics and Spectroscopy, Sep./1975, Bd. 39, Nr. 3, pp. 338–339).

Primary Examiner—Michael Peffley
Assistant Examiner—A. Farah
(74) Attorney, Agent, or Firm—Reed Smith LLP

(57) ABSTRACT

A device for the ablation of biological substances by laser radiation, especially for stomatologic treatment, comprises a pump laser and a laser converter for converting the pump laser radiation into a laser radiation having the wavelength range of 3 μm±0.2 μm, wherein the laser converter is accommodated in a treatment head which is separated from the pump laser by a fiber-optic device. There is provided in the laser converter a metal-holmium-fluoride crystal with an alkaline or alkaline-earth ion as metal ion with partial substitution of the holmium (Ho) ions, namely one of the following compounds: $Me(Ho_{1-x}Pr_x)F_4$ with a metal ion of lithium (Li) or sodium (Na), a fluorine ion, and with components of praseodymium of x=0.001 to 0.03, or $Ba(Ho_{1-x}Pr_x)_2F_8$, where Ba is a barium ion, F is a fluorine ion, and with components of praseodymium of x=0.0005 to 0.015.

8 Claims, 1 Drawing Sheet

U.S. PATENT DOCUMENTS

| | | | |
|---|---|---|---|
| 5,552,373 | * | 9/1996 | Agostinelli et al. .................. 505/190 |
| 5,568,503 | * | 10/1996 | Omari ..................................... 372/70 |
| 5,644,584 | * | 7/1997 | Nam et al. ............................. 372/20 |
| 5,739,554 | * | 4/1998 | Edmond et al. ..................... 257/103 |
| 5,785,703 | * | 7/1998 | Goodman et al. ..................... 606/10 |
| 5,846,080 | * | 12/1998 | Schneider ............................. 433/215 |
| 5,954,710 | * | 9/1999 | Poalini et al. .......................... 606/7 |
| 6,120,600 | * | 9/2000 | Edmond et al. ....................... 117/89 |

* cited by examiner

DEVICE FOR ABLATION OF MATERIAL BY MEANS OF LASER RADIATION

BACKGROUND OF THE INVENTION a) Field of the Invention

The invention is directed to a device for the ablation of material by means of laser radiation, especially for treatment of biological substances in stomatologic, endoscopic, dermatologic, rhinoplastic and the like procedures, comprising a pump laser for generating a radiation-exciting laser radiation and comprising a laser converter for converting the pump laser radiation into a laser radiation that is provided for treatment in the wavelength range of 3 $\mu$m±0.2 $\mu$m, wherein the laser converter is accommodated in a treatment head which is spatially separated from the pump laser, and wherein a fiber-optic device is provided for transmitting laser radiation from the pump laser to the laser converter.

b) Description of the Related Art

Devices of the type mentioned above belong, in principle, to the prior art and are known, for example, from DE OS 4341108 and EP 0530574. DE OS 4341108 describes a two-stage laser system for hard-tissue surgery in which the radiation of a first laser is transmitted, via an optical waveguide, to a second, miniaturized laser crystal and is used therein for coaxial pumping of this miniaturized laser crystal. The pump laser is a pulsed diode laser with an emission wavelength between 900 nm and 1000 nm. A fused-quartz fiber is used to transmit the pump laser radiation. The second laser which emits the actual working radiation is a rod-shaped erbium-yttrium-aluminum-garnet laser crystal. This YAG laser is arranged directly in a handpiece from which the working radiation can be directed to the hard dental tissue, namely at a wavelength in the range of 3 $\mu$m.

Three different variants are indicated for the arrangement of the pump laser and the arrangement of the laser inserted in the handpiece. A first variant provides for the use of a Nd:YAG laser with a pulse energy of approximately 2 Joules and a pulse width of about 1 ms to 50 ms. This YAG radiation is transmitted via a fused-quartz fiber with a core diameter of approximately 80 $\mu$m to an Er:YAG laser crystal arranged in the handpiece. The Er:YAG crystal is doped with ytterbium atoms. In a second embodiment form, a Nd:YAG laser emitting a wavelength of 1.44 $\mu$m is used as pump radiation source. The 1.44-$\mu$m radiation is again transmitted through a fused-quartz fiber to the dental handpiece and is used for pumping an Er:YGD laser crystal. In the third embodiment form, laser radiation is first generated with a wavelength of 2.65 $\mu$m to 2.69 $\mu$m and is transmitted via extremely anhydrous fused-quartz fibers in the handpiece and used for pumping an Er:YAG laser crystal.

A disadvantage in all of the suggested solutions consists in the very high thermal losses in the conversion of the pump radiation into the working radiation which must be compensated through relatively large geometric dimensions of the laser crystal in the handpiece. Therefore, the handpiece in which the laser crystal is integrated must necessarily also have large dimensions. Further, the output losses require that the pump laser radiation must be transmitted with very high intensity through the optical fiber to the handpiece, which leads to overloading of currently available optical fiber materials, so that their possible useful life is reduced to an undesirable extent.

The second reference cited above proposes a process and a device for ablation of biological hard substance, especially hard dental substance, which use a short pulsed laser in the wavelength range between 2.78 $\mu$m and 2.94 $\mu$m. Further, means are provided which even out the intensity time response of the laser radiation, so that transmittability via the optical waveguide is improved.

The short pulsed laser is accommodated in the handpiece as a solid-state laser. A Cr-Er-doped YSGG (yttrium-scandium-gadolinium-garnet) crystal is preferably used as laser crystal. Alternatively, it is suggested to use an Er:YAG laser which emits radiation in the wavelength range of 2.96 $\mu$m. This makes use of the fact that the absorption maximum of the target substance shifts dynamically toward shorter wavelengths because of the absorption process during the active period of the pulsed laser radiation itself. When treating hard dental substance, for example, the absorption maximum of water-containing hard dental substance (hydroxyapatite) shifts from approximately 3 $\mu$m to approximately 2.8 $\mu$m. The transmittability of the pump laser radiation via optical fibers to the laser crystal in the handpiece is improved in that an additional crystal with light-linear optical characteristics is placed in the beam waist of the laser, either inside or outside of the resonator. According to the reference, lithium iodate or silver-gallium-sulfide is used for this crystal.

In addition, optical steps are provided for reducing the radiation loss and accordingly the output loss in comparison with the prior art, e.g., the formation of the resonator from 2 confocal mirrors, between which a laser-active medium (gas, liquid, solid or semiconductor) is arranged. The crystal for smoothing the intensity time response is arranged inside the resonator.

This suggestion still has the disadvantage of high output losses calling for excessively large geometric dimensions of the laser converter and accordingly also of the handpiece, so that additional areas of application in medicine, e.g., ablation not only in the field of stomatology but also in endoscopic laser therapy, rhinoplasty, etc., could not be fully developed.

However, it is desirable that these areas be developed because it is known that not only hard biological substances such as hard dental tissue, but also other materials containing $H_2O$ and OH groups show an absorption maximum of radiation in the wavelength range of 2.8 $\mu$m to 3.1 $\mu$m and can be treated by means of this radiation effectively and without negative secondary effects, since laser treatment at a wavelength of 3 $\mu$m has the decisive advantage over treatment at other wavelengths that the penetration depth is smaller and the negative effect on deeper layers is reduced. When the geometric dimensions of the handpiece are reduced, additional very useful possibilities for application beyond the aforementioned areas of human medicine extend to veterinary medicine and, finally, in general, to the treatment of other organic and inorganic materials under difficult conditions of access.

Thus, there is an extensive need to open up these areas of application with respect to technical instrumentation. While the exciting laser radiation can be transmitted along sufficiently long lengths to a treatment head in the aforementioned solutions through available fused-quartz fibers, it is necessary, in order to make the device usable for the above-mentioned areas of application, that the laser crystal in the laser converter and the treatment head in which the laser converter is accommodated are produced with sufficiently small dimensions while retaining a sufficiently high laser output, which in turn only succeeds when the device has a very high efficiency or when the thermal losses in the laser converter can be kept very low. Therefore, the energy efficiency of the laser crystal in the laser converter becomes a decisive characteristic.

OBJECT AND SUMMARY OF THE INVENTION

Therefore, the primary object of the invention is to further develop a device for the ablation of material by means of laser radiation of the type described above in such a way that the use of smaller laser crystals in the laser converter is made possible by increasing the efficiency in the conversion of the pump laser radiation into radiation with a wavelength in the range of 3 $\mu m \pm 0.2$ $\mu m$.

According to the invention, this object is met for a device for the ablation of material by means of laser radiation in that there is provided in the laser converter a metal-holmium-fluoride crystal with an alkaline or alkaline-earth ion as metal ion with partial substitution of the holmium (Ho) ions by praseodymium (Pr) ions, namely one of the following compounds:

Me(Ho$_{1-x}$Pr$_x$)F$_4$, where Me is a metal ion of lithium (Li) or sodium (Na), F is a fluorine ion, and with atomic components of praseodymium of x=0.001 to 0.03, or Ba(Ho$_{1-x}$Pr$_x$)$_2$F$_8$, where Ba is a barium ion, F is a fluorine ion, and with atomic components of praseodymium of x=0.0005 to 0.015.

It is provided in advantageous developments of the invention that the crystal of the pump laser alternatively comprises neodymium-doped yttrium-aluminum-garnet Y$_3$Al$_5$O$_{12}$:Nd with an emission wavelength of the pump laser radiation of 1.12 $\mu$m, neodymium-doped yttrium orthoaluminate YAlO$_3$:Nd with an emission wavelength of the pump laser radiation of 1.08 $\mu$m, or a laser diode with an emission wavelength in the range of 1.1 to 1.15 $\mu$m is used as a pump laser.

A further solution of the invention provides that a metal-holmium-fluoride crystal with an alkaline or alkaline-earth ion as metal ion with partial substitution of the holmium (Ho) ions by praseodymium (Pr) ions and further with partial substitution of the holmium (Ho) ions by ions of the rare earths ytterbium (Yb) or yttrium (Y) is provided, namely one of the following compounds:

Me(Ho$_{1-x-y}$Pr$_x$RE$_y$)F$_4$, where Me is a metal ion of lithium (Li) or sodium (Na), RE is an ion of ytterbium (Yb) or yttrium (Y), F is a fluorine ion, with components of praseodymium of x=0.001 to 0.03 and with atomic components of ytterbium (Yb) or yttrium (Y) of y=0.2 to 0.9, or Ba(Ho$_{1-x-y}$Pr$_x$RE$_y$)$_2$F$_8$, where Ba is a barium ion, F is a fluorine ion, RE is an ion of ytterbium (Yb) or yttrium (Y), with components of praseodymium of x=0.0005 to 0.015, and with atomic components of ytterbium (Yb) or yttrium (Y) of y=0.1 to 0.45.

In embodiment variants of this invention, it is provided that the crystal of the pump laser comprises neodymium-doped yttrium-lithium-fluoride YLiF$_4$:Nd with an emission wavelength of the pump laser radiation of 1.047 $\mu$m, or that a laser diode with an emission wavelength in the range of 0.93 to 0.98 $\mu$m is provided as pump laser.

The essential advantage of the invention consists in that the geometric dimensions of the treatment head can be substantially reduced. At the same time this results in a drastic reduction in costs for the electronic powering of the pump laser. Expenditure on cooling in the laser converter is likewise reduced or entirely obviated.

The use of a crystal of this kind with the indicated doping causes an appreciable reduction in output loss during conversion of the pumped radiation into the effective or working radiation of the wavelength in the 3-$\mu$m range. This can be explained in that it was possible in this way to utilize direct absorption transitions of the holmium ion for the radiation emitted by the pump laser in the crystals in the laser converter having the specified compositions Me(Ho$_{1-x}$Pr$_x$)F$_4$, where Me=lithium or sodium and Me(Ho$_{1-x-y}$Pr$_x$Y$_y$)$_2$F$_8$, where Me=barium. As a result of the selection of the holmium-fluoride as basis (main component) for the laser converter crystal, the radiation occurring during recombination at the holmium is in the required range of 2.9±0.2 $\mu$m. The real laser converter wavelength within this range occurs as a function of the metal ion. The components suggested according to the invention in the composition of the crystal ensure a very high energy conversion coefficient with an energy transmission velocity at which the parasitic processes leading to energy loss cannot even begin to develop.

The inclusion of praseodymium in the crystal lattice reduces the lifetime of the lower level $^5I_7$ of the holmium ion so that the relative inversion population density of the transition $^5I_5$–$^5I_7$ is increased and the efficiency is accordingly further improved. This effect is negligible at a praseodymium concentration below a certain limit, and at a praseodymium concentration above 0.03 this leads to the parasitic absorption of the radiation of the pump laser.

In crystals with the composition Me(Ho$_{1-x}$Pr$_x$)F$_4$, where Me=lithium or sodium, and Me(Ho$_{1-x-y}$Pr$_x$Y$_y$)F$_4$, where Me=barium, the absorption coefficient is roughly 2 cm$^{-1}$. This permits the dimensions of the laser converter to be reduced to a diameter of 0.5 to 1 mm and a length of 4 to 6 mm and accordingly makes it possible to open up the broad range of endoscopic applications at, for these cases, sufficient pulse frequency and medium output also in CW and QCW modes.

In order to further increase the energy and output of the radiation, a portion of the holmium ions is replaced isomorphically, according to the invention, by yttrium ions which have no absorption in the range of 1.08 to 1.15 $\mu$m. This reduces the absorption coefficient of the pump laser radiation and makes it possible to increase the length of the laser converter and, therefore, to improve heat removal and, in turn, increase efficiency. A reduction in the yttrium component below 0.2 causes only a negligible reduction in the absorption of the pump laser radiation and an increase of y over 0.9 leads to a reduction in efficiency because the quantity of excitable holmium ions is reduced too drastically.

In the crystals having the composition Me(Ho$_{1-x-y}$Pr$_x$Y$_y$)F$_4$, a portion of the holmium ions is replaced isomorphically, according to the invention, by ytterbium ions which possess a good absorption in the range of 0.93 to 1.05 $\mu$m, wherein there is a series of very effective pump lasers in this range. The energy absorbed by the ytterbium ions is transferred to the holmium ions (indirect excitation).

In this case, the efficiency of the entire pump laser-converter system is determined by the available highly effective pump lasers for this range. An excessive reduction in the ytterbium content results, for example, in an undesirably large reduction in the absorption of the pump laser radiation. An excessive increase reduces the efficiency of the laser converter.

In a very advantageous configuration of the invention, the laser crystal in the laser converter is shaped spherically with a radius of curvature between 0.3 and 1.5 m at its end facing the pump laser, and mirrors are arranged at both ends of this laser crystal to form a laser resonator for the wavelength range of 3±0.2 $\mu$m, wherein the mirror on the side facing the pump laser is highly reflecting for the wavelength range of 3±0.2 μm and highly transmitting for the pump laser radiation, and the mirror arranged on the opposite end is partially transmitting for the wavelength range of 3±0.2 μm and highly reflecting for the pump laser radiation. This enables an even simpler construction of the laser converter which is easily accommodated in the treatment head due to its small structural dimensions. Moreover, efficiency is increased still further by the reduction of parasitic losses for the 3-μm radiation at the mirrors and by the reduction in adjustment sensitivity in the assembly and operation of the laser.

As an alternative to solid state lasers which are provided in accordance with the above description for generating a pump laser radiation with wavelengths 1.047 μm, 1.08 μm and 1.12 μm, the pumped radiation can, of course, also be generated by laser-active media in the form of gases, liquids or semiconductors and its radiation can be utilized for exciting the laser converter.

BRIEF DESCRIPTION OF THE DRAWINGS

The invention will be described more fully hereinafter with reference to an embodiment example.

Figure 1:
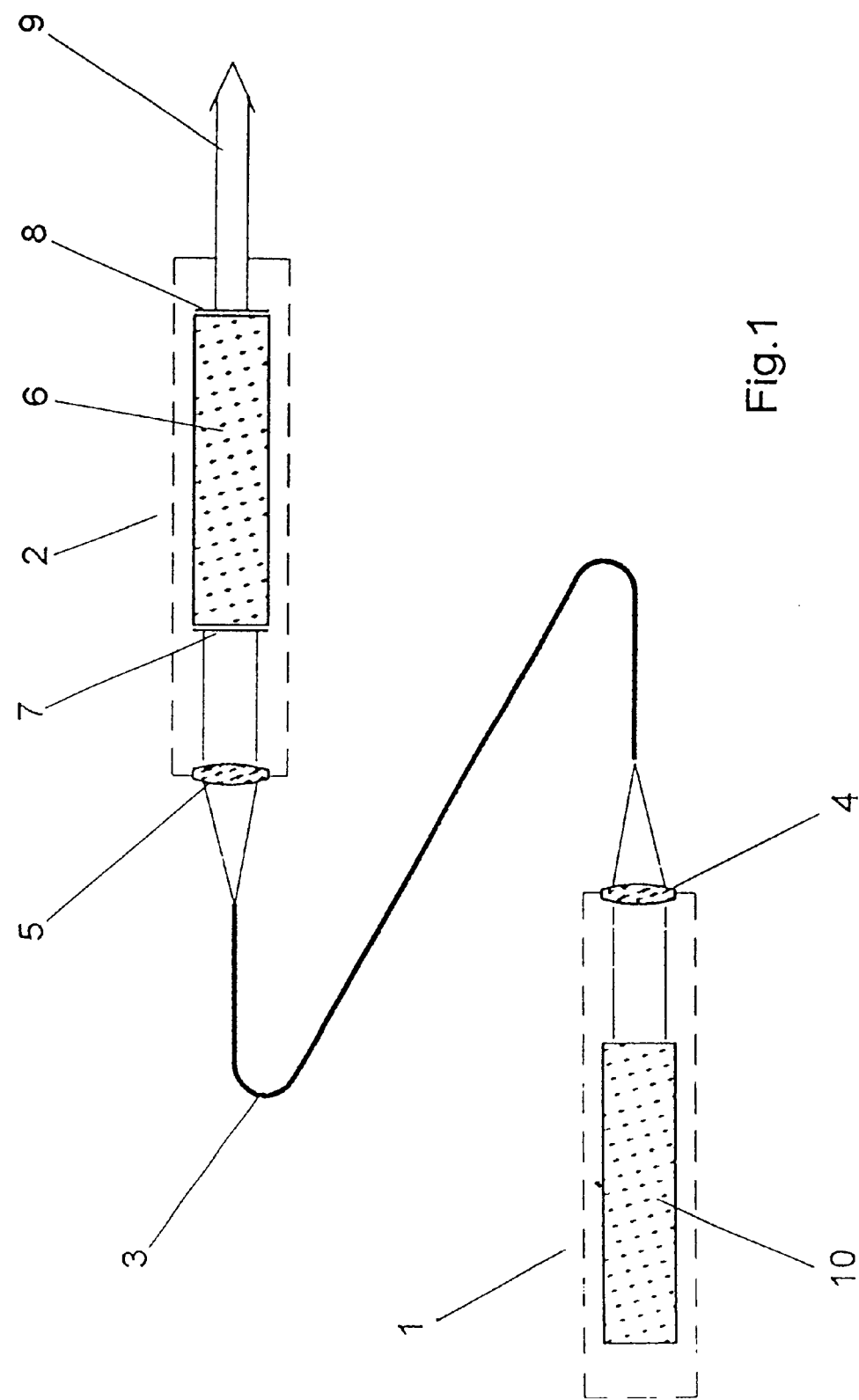
In FIG. 1, the accompanying drawing shows the basic construction of the device according to the invention.

While the foregoing description and drawings represent the present invention, it will be obvious to those skilled in the art that various changes may be made therein without departing from the true spirit and scope of the present invention.

DESCRIPTION OF THE PREFERRED EMBODIMENT

FIG. 1 shows a pump laser 1 and a laser converter 2 which are connected with one another by an optical waveguide 3. Imaging optics 4 are arranged at the radiative transitions from the pump laser 1 to the light waveguide 3; coupling optics 5 are also arranged at the radiative transition from the light waveguide 3 to the laser converter 2. The end face of the laser crystal 6 facing the light waveguide 3 in the laser converter 2, i.e., its input-coupling end, is mirrored, e.g., with a plane mirror surface 7. Alternatively, a spherically curved surface with a radius of between 0.3 m and 1.5 m can be advantageous for this purpose. The opposite, output-coupling end of the laser crystal 6 is constructed in an analogous manner as a mirror surface 8. The two mirror surfaces 7, 8 are arranged on the laser crystal 6 as layer systems and serve as resonator mirrors. In this respect, the mirror surface 7 has a high transparency for the pump laser wavelength, for example, 1.12 μm, and high reflection for wavelengths 2.8 μm to 3.1 μm. The opposite mirror surface 8, on the other hand, which serves for coupling out the effective or working radiation 9 is formed by a layer system which is partially transparent for wavelengths from 2.8 to 3.1 μm and which, at the same time, is highly reflecting for the radiation emitted by the pump laser.

A neodymium-doped yttrium-aluminum-garnet laser $Y_3Al_5O_{12}$:Nd with an emission wavelength of the pump laser radiation of 1.12 μm is provided, for example, as crystal 10 in the pump laser 1. A multiple-component crystal with a metal ion and an alkaline or alkaline-earth fluoride with elements holmium (Ho) and praseodymium (Pr), namely, the compound $Ba(Ho_{1-x}Pr_x)_2F_8$, where x=0.0005 to 0.015, is provided as laser crystal 2.

A simple structure of the laser converter as a precondition for an advantageous structural design of the treatment head with very small dimensions is achieved by means of this device which also enables complicated tissue treatment to be used within broad areas of application.

What is claimed is:

1. A device for the ablation of material by laser radiation, especially for treating biological substances in stomatologic, endoscopic, dermatologic, rhinoplastic and the like procedures, comprising:

a pump laser for generating a radiation-exciting laser radiation;

a laser converter for converting the pump laser radiation into a laser radiation that is provided for the treatment having the wavelength range of 3 μm±0.2 μm;

said laser converter is accommodated in a treatment head which is spatially separated from the pump laser;

a fiber-optic device being provided for transmitting laser radiation from the pump laser to the laser converter using direct absorption transitions; and a metal-holmium-fluoride crystal with an alkaline or alkaline-earth ion as metal ion with partial substitution of the holmium (Ho) ions by praseodymium (Pr) ions, namely one of the following compounds:

$Me(Ho_{1-x}Pr_x)F_4$, where Me is a metal ion of lithium (Li) or sodium (Na), F is a fluorine ion, and with atomic components of praseodymium of x=0.001 to 0.03, or $Ba(Ho_{1-x}Pr_x)_2F_8$, where Ba is a barium ion, F is a fluorine ion, and with atomic components of praseodymium of x=0.0005 to 0.015, being provided as laser crystal in the laser converter.

2. The device for the ablation of material by laser radiation according to claim 1, wherein the crystal of the pump laser comprises neodymium-doped yttrium-aluminum-garnet $Y_3Al_5O_{12}$:Nd and the emission wavelength of the pump laser radiation is 1.12 μm.

3. The device for the ablation of material by laser radiation according to claim 1, wherein the crystal of the pump laser comprises neodymium-doped yttrium orthoaluminate $YAlO_3$:Nd and the emission wavelength of the pump laser radiation is 1.08 μm.

4. The device for the ablation of material by laser radiation according to claim 1, wherein a laser diode with an emission wavelength in the range of 1.1 to 1.15 μm is provided as pump laser.

5. A device for the ablation of material by laser radiation, especially for treating biological substances in stomatologic, endoscopic, dermatologic, rhinoplastic and the like procedures, comprising:

a pump laser for generating a radiation-exciting laser radiation;

a laser converter for converting the pump laser radiation using direct absorption transitions into a laser radiation that is provided for the treatment having the wavelength range of 3 μm±0.2 μm;

said laser converter is accommodated in a treatment head which is spatially separated from the pump laser; and a fiber-optic device being provided for transmitting laser radiation from the pump laser to the laser converter comprising a metal-holmium-fluoride crystal with an alkaline or alkaline-earth ion as metal ion with partial substitution of the holmium (Ho) ions by praseodymium (Pr) ions and further with partial substitution of the holmium (Ho) ions by ions of the rare earths ytterbium (Yb) or yttrium (Y) is provided as laser crystal in the laser converter, namely one of the following compounds:

$Me(Ho_{1-x-y}Pr_xRE_y)F_4$, where Me is a metal ion of lithium (Li) or sodium (Na), RE is an ion of ytterbium (Yb) or yttrium (Y), F is a fluorine ion, with components of praseodymium of x=0.001 to 0.03 and with components of ytterbium (Yb) or yttrium (Y) of y=0.2 to 0.9, or $Ba(Ho_{1-x-y}Pr_xRE_y)_2F_8$, where Ba is a barium ion, F is a fluorine ion, RE is an ion of ytterbium (Yb) or yttrium (Y), with components of praseodymium of x=0.0005 to 0.015, and with components of ytterbium (Yb) or yttrium (Y) of y=0.1 to 0.45.

6. The device for the ablation of material according to claim 5, wherein the crystal of the pump laser comprises neodymium-doped yttrium-lithium-fluoride $YLiF_4$:Nd and the emission wavelength of the pump laser radiation is 1.047 μm.

7. The device for the ablation of material according to claim 5, wherein a laser diode with an emission wavelength in the range of 0.93 to 0.98 μm is provided as pump laser.

8. The device for the ablation of material by laser radiation according to claim 5, wherein the laser crystal in the laser converter is shaped spherically with a radius of curvature between 0.3 and 1.5 m at its end facing the pump laser, and in that mirrors are arranged at both ends of this laser crystal and form a laser resonator for the wavelength range of 3±0.2 μm, wherein the mirror on the side facing the pump laser is highly reflecting for the wavelength range of 3±0.2 μm and highly transmitting for the pump laser radiation, and the mirror arranged on the opposite end is partially transmitting for the wavelength range of 3±0.2 μm and highly reflecting for the pump laser radiation.

* * * * *